(12) United States Patent
Amano et al.

(10) Patent No.: US 10,071,189 B2
(45) Date of Patent: Sep. 11, 2018

(54) MEDICAL APPARATUS WITH LUBRICITY AND MANUFACTURING METHOD OF SAME

(75) Inventors: Kenichi Amano, Shizuoka (JP); Miki Muramatsu, Shizuoka (JP)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/402,082

(22) Filed: Feb. 22, 2012

(65) Prior Publication Data

US 2012/0253296 A1    Oct. 4, 2012

(30) Foreign Application Priority Data

Mar. 30, 2011  (JP) ................. 2011-075633

(51) Int. Cl.
| | |
|---|---|
| A61M 25/00 | (2006.01) |
| A61M 5/32 | (2006.01) |
| A61L 31/02 | (2006.01) |
| A61L 31/08 | (2006.01) |
| A61M 25/09 | (2006.01) |
| C08L 63/00 | (2006.01) |

(52) U.S. Cl.
CPC ........... *A61L 31/022* (2013.01); *A61L 31/082* (2013.01); *A61M 25/09* (2013.01); *C08L 63/00* (2013.01); *A61L 2400/10* (2013.01); *A61M 2025/09108* (2013.01); *A61M 2025/09133* (2013.01)

(58) Field of Classification Search
CPC ............... A61L 2400/10; C08L 63/00; A61M 2025/09108; A61M 2025/09133; A61M 25/09
USPC ................................ 604/265–269
See application file for complete search history.

(56) References Cited

U.S. PATENT DOCUMENTS

| | | | |
|---|---|---|---|
| 5,069,899 A | 12/1991 | Whitboume et al. | |
| 5,783,570 A | 7/1998 | Yokota et al. | |
| 2004/0086568 A1 | 5/2004 | Ditizio et al. | |
| 2006/0041204 A1* | 2/2006 | Kato | A61M 25/09 600/585 |
| 2008/0091168 A1* | 4/2008 | Amano et al. | 604/523 |
| 2009/0318746 A1* | 12/2009 | Thurmond et al. | 600/8 |

FOREIGN PATENT DOCUMENTS

| | | |
|---|---|---|
| CN | 1250382 A | 4/2000 |
| CN | 101146558 A | 3/2008 |
| JP | 63098384 | 4/1988 |
| JP | 10155898 | 6/1998 |
| JP | 10165493 | 6/1998 |
| JP | 10248918 | 9/1998 |
| JP | 10295799 | 11/1998 |
| JP | 10328293 | 12/1998 |
| JP | 11290449 | 10/1999 |
| JP | 2002179861 | 6/2002 |
| JP | 2003225300 | 8/2003 |
| JP | 2003299725 | 10/2003 |
| JP | 2003299726 | 10/2003 |
| JP | 2005103238 | 4/2005 |
| KR | 20070108278 A | 11/2007 |
| WO | 98/32474 A1 | 7/1998 |
| WO | 199832474 A1 | 7/1998 |
| WO | 2006094521 A1 | 9/2006 |
| WO | WO 2006/094521 | 9/2006 |
| WO | WO 2008/082493 A1 | 7/2008 |

OTHER PUBLICATIONS

International Search Report issued in corresponding European Application No. 12159920.3-1219 dated Sep. 6, 2012.
European Search Report, Application No. 07118192.9-1219, dated Feb. 25, 2008, 6 pages.
European Office Action cited in corresponding Application No. EP 07 118 192.9 dated Feb. 18, 2009, 5 pages.
Office Action dated Nov. 15, 2013 issued in Chinese Appl. No. 201210153742.9.
Office Action issued in Korean Application No. 10-2012-32496 dated Dec. 30, 2013.
Notification of Reexamination, and translation thereof, from counterpart Chinese Application No. 201210153742.9, dated Aug. 18, 2015, 22 pp.
Ping et al., "Polymer Materials Science," Chemical Industry Press, Aug. 2010, 2th Edition, 1st Print, pp. 73-74; (Machine Translation of description of book introduction and summary, Translation of pages not available).
Notification of Reexamination, and translation thereof, from Counterpart Chinese Patent Application No. 201210153742.9, dated Jan. 5, 2015, 15 pp.

\* cited by examiner

*Primary Examiner* — Rebecca E Eisenberg
(74) *Attorney, Agent, or Firm* — Shumaker & Sieffert, P.A.

(57) ABSTRACT

The present disclosure provides a medical instrument with a coating that provides excellent lubricity when wet. The medical instrument possesses a coating including a wet lubricating film with high peel durability and anti-eluting properties. In embodiments, an intermediate film made of bisphenol A type epoxy resin is coated on a base material of a medical instrument made of metal, and a wet lubricant coating produced by alkaline processing of a polymer alloy containing a methyl vinyl ether maleic anhydride copolymer and a polyether block amide is then applied thereto. Methods for making these medical instruments are also provided.

21 Claims, No Drawings

MEDICAL APPARATUS WITH LUBRICITY AND MANUFACTURING METHOD OF SAME

CROSS-REFERENCE TO RELATED APPLICATION

This application claims the benefit of and priority to Japanese Application No.: 2011-075633 filed Mar. 30, 2011, the entire disclosure of which is incorporated by reference herein.

TECHNICAL FIELD

The present disclosure relates to lubricious medical instruments and methods for manufacturing same. In accordance with the present disclosure, a lubricious film is provided on at least a portion of a surface of a medical instrument, where the film possesses lubricity when wet. In embodiments, the instrument may be made of metal, and may be a guide wire or the like.

BACKGROUND

Some medical instruments, such as guide wires and needles that are used to help insert catheters, are inserted and left in blood vessels, respiratory tracts, urinary tracts, and other body cavities and tissues. When these medical instruments are inserted, the surface of the medical instrument should easily slide in order to avoid injuring tissue membranes and causing inflammation, as well as to relieve any pain experienced by the patient receiving the treatment.

Therefore, some medical instruments are provided with lubricity, which may be provided by applying a silicone oil, glycerin, or the like to the surface, as an innovation for enhancing sliding and reducing friction resistance. These medical instruments can easily be manufactured by dipping the medical instrument in a solution containing silicone oil or the like, or by spraying silicone oil or the like, and therefore this technique is suitable for a broad range of medical instruments.

Furthermore, some medical instruments, such as catheters made of synthetic resin, have a film formed thereon by applying onto the base material surface a solution including a methyl vinyl ether maleic anhydride copolymer and a polyether block amide dissolved in an organic solvent. Such a film coating may demonstrate excellent lubricity when wet. When the medical instrument is inserted into a body cavity, tissue, or the like, the surface of the medical instrument is moistened by the moisture in the body. Furthermore, the portion of the surface of the medical instrument where a film is formed will demonstrate lubricity with a slippery feel, and thus the surface of the medical instrument will easily slide. Therefore, when the medical instrument is inserted into a body cavity or the like, the practitioner, such as a doctor, will be able to easily insert the medical instrument.

In some cases, for medical instruments that possess lubricity from a film formed of a silicone oil, glycerin, or the like, the film can easily be removed by rubbing the region with lubricity by hand. Thus, providing lubricity using these films may not be suitable for medical instruments that are required to have peeling resistance of the lubricity.

Furthermore, for base materials made of metals, including guide wires, the adhesion of the film towards metal is greatly reduced, and as a result the lubrication layer or film may peel off or elute into physiological saline solution, or the like, when used for a long period of time or when used multiple times, and thus the lubricity is reduced.

Medical instruments with lubricity that have excellent peel durability and anti-eluting properties, and that can demonstrate excellent lubricity when wet, over a long period of time, remain desirable.

SUMMARY

The present disclosure provides medical instruments and methods for making these instruments. In embodiments, a medical instrument according to the present disclosure includes a base material made of metal. The medical instrument includes an intermediate film that covers at least a part of the base material surface. In embodiments, the intermediate film includes a bisphenol A type epoxy resin produced by reacting a bisphenol A epoxy resin prepolymer and a polyamide amine curing agent.

The medical instrument further includes a lubricant layer or film formed on the intermediate film. The lubricant layer or film, in embodiments, is synthesized by alkali treatment of a polymer alloy of a methyl vinyl ether maleic anhydride copolymer and a polyether block amide.

In embodiments, the metal used to form the base material of a medical instrument of the present disclosure is stainless steel.

In some embodiments, the medical instrument according to the present disclosure is a guide wire.

Methods according to the present disclosure for manufacturing a medical instrument having lubricity include applying a mixture solution for forming an intermediate film, the solution including a bisphenol A type epoxy resin prepolymer and a polyamide amine-type curing agent in xylene and 1-butanol. The solution for forming the intermediate film is placed onto at least a part of a surface of a medical instrument made of metal, and then heated to form an intermediate film made of bisphenol A type epoxy resin. The method then includes applying to the medical instrument a mixture solution for forming a wet lubricant film, the solution for the wet lubricant film including a solvent such as acetone in combination with methyl vinyl ether maleic anhydride copolymer, and a tetrahydrofuran solution of a polyether block amide, and then alkali processing the solution to form a wet lubricant film.

DETAILED DESCRIPTION

The present disclosure provides methods for forming medical instruments having a wet lubricant film coating, and medical instruments possessing such a film coating. The wet lubricant film has excellent lubricity when wet, so the medical instrument will easily slide and can be smoothly inserted into body cavities and tissue. As a result, an operation of inserting the medical instrument can be easily performed by a practitioner, such as a doctor, or the like. In addition, when the medical instrument is inserted, the insertion can be performed without applying excessive force to the medical instrument, and therefore the possibility of injuring areas other than the body insertion area is reduced and the safety is enhanced.

In embodiments, the medical instrument with lubricity according to the present disclosure contains a base material made of metal; an intermediate film that covers at least a part of the base material surface, in embodiments including a bisphenol A type epoxy resin produced by reacting a bisphenol A epoxy resin prepolymer and a polyamide amine curing agent; and a wet lubricant formed on the intermediate film, the wet lubricant synthesized by alkali treatment of a polymer alloy of a methyl vinyl ether maleic anhydride copolymer and a polyether block amide.

The medical instrument made of metal in accordance with the present disclosure can be a variety of products such as a guide wire, needle, stylet, or the like. Where the instrument is a guide wire, the lubricity can be most effectively demonstrated, and the properties of inserting into a body cavity or tissue, push in properties, tracking properties, and kink resistant properties, as well as the resilience of these properties, can be enhanced with the film coatings of the present disclosure.

The material that forms the base material of the medical instrument can be a variety of metals such as stainless steel, steel, copper, aluminum, combinations thereof, and the like. For stainless steel, in particular, the bonding properties of the wet lubricant film to the base material are enhanced by the intermediate film, and the lubricity can be effectively demonstrated.

The medical instrument of the present disclosure, having lubricity, has an intermediate film. The intermediate film has excellent adhesion to the base materials made of metal, which are used to form the medical instrument, and the intermediate film also has excellent bonding properties with the wet lubrication film. Therefore, the peeling durability of the wet lubricant film will be high, and the anti-eluting properties, when left in blood, body fluid or the like, will be enhanced. Therefore, the lubricity of the medical instrument made of metal can be maintained, and its use can be continued without replacing the instrument with a new instrument, even when used for a long period of time or when repeated use is required.

In embodiments, the intermediate film includes an epoxy resin. An epoxy resin is a general name for compounds with two or more oxirane rings (epoxy groups), and an epoxy resin can be produced by reacting a curing agent with an epoxy resin prepolymer.

In embodiments, a bisphenol A type epoxy resin prepolymer is used as an epoxy resin prepolymer, and a polyamide amine-type curing agent is used as a curing agent. A bisphenol A type epoxy resin prepolymer is synthesized from bisphenol A and epichlorohydrin (2-chloromethyloxirane), and is used as a material for synthesizing the intermediate film of the present disclosure.

The curing agent for the epoxy resin prepolymer is a polyamide amine-type curing agent. Polyamide amine is synthesized by a condensation reaction between a dimer acid and polyamine, and generally refers to compounds with a reactive primary amine group or secondary amine group in the molecule.

Bisphenol A type epoxy resins are synthesized by a condensation reaction between the bisphenol A type epoxy resin prepolymer and the polyamide amine-type curing agent. The blending ratio of the bisphenol A type prepolymer and the polyamide amine-type curing agent can be any ratio, so long as there is sufficient curing capability to synthesize the bisphenol A type epoxy resin.

The intermediate film coating formed on a medical instrument of the present disclosure is synthesized by dissolving and diluting the bisphenol A type prepolymer and the polyamide amine-type curing agent in a mixed solution of xylene and 1-butanol. The mixture solution of xylene and 1-butanol is a solvent with excellent solubility and can quickly dissolve the bisphenol A type prepolymer and the polyamide amine-type curing agent in a short period of time, and can favorably promote the reaction between the bisphenol A type prepolymer and the polyamide amine-type curing agent.

The intermediate film made of bisphenol A type epoxy resin can be coated on the medical instrument by applying a solution including the components of the intermediate film coating onto the surface of the metal base material of the medical instrument, and then heating. The method of applying the solution for forming intermediate film coating may be, in embodiments, a dipping process where the medical instrument is gradually immersed in the mixture solution for forming the intermediate film coating, and then gradually lifting the base material out of the solution. Thereby, an intermediate film with essentially a uniform thickness can be applied to the required areas on the surface of the base material of the medical instrument. Other suitable methods for application of the solution for forming the intermediate film coating include, for example, by any other suitable method such as applying the solution using a brush, or by spraying the solution onto the surface of the base material of the medical instrument as a spray.

Furthermore, the base material of the medical instrument that has been coated with the solution for forming the intermediate film coating is heated to a temperature from about 50° C. to about 100° C. Thereby, the bisphenol A type prepolymer and the polyamide amine-type curing agent of the solution for forming the intermediate film coating will react to synthesize the bisphenol A type epoxy resin. The solvent is then removed, and as a result, a film of bisphenol A type epoxy resin will be formed on the surface of the base material of the medical instrument. Note, the heating temperature should be within from about 50° C. to about 100° C. in order to prevent deformation of the guide wire, in embodiments from about 70° C. to about 90° C. Furthermore, the heating time is not particularly restricted, and is determined in combination with the heating temperature. If the heating temperature is from about 70° C. to about 90° C., the heating time is from about 2 hours to about 4 hours.

A layer of wet lubricant is then formed on the intermediate film coating. In embodiments, the lubricant includes a polymer alloy of a methyl vinyl ether maleic anhydride copolymer and a polyether block amide.

The methyl vinyl ether maleic anhydride copolymer is a copolymer polymerized from monomer units where methyl vinyl ether and maleic anhydride are covalently bonded, and has physical properties that can dissolve in alcohols, esters, ketones, glycol ethers, and the like. In accordance with the present disclosure, the methyl vinyl ether maleic anhydride copolymer is dissolved in acetone, to form an acetone solution of the methyl vinyl ether maleic anhydride copolymer. Furthermore, the concentration of the solution is suitably from about 0.5 to about 5 percent by weight, in embodiments from about 1 to about 3 percent by weight.

The polyether block amide is a copolymer obtained by polymerizing monomer units containing covalently bonded hard segments of polyamide and soft segments of polyether. The polyamide and the polyether can form various molecular structures, and therefore there is a rich variety of polyether block amides. The polyether block amide has properties that dissolve in ketones and the like, such as cyclohexanone and tetrahydrofuran (hereinafter abbreviated as "THF"). In accordance with the present disclosure, the polyether block amide can be dissolved in THF, but any solvent can be used so long as the aforementioned dissolving can be achieved. Furthermore, the concentration of the solution is from about 0.5 to about 5 percent by weight, in embodiments from about 1 to about 3 percent by weight.

The mixture solution for forming a wet lubricant film is made by blending the THF solvent of the polyether block amide and the acetone solution of the methyl vinyl ether maleic anhydride copolymer, manufactured by the aforementioned methods. The blending ratio of the acetone solution of methyl vinyl ether maleic anhydride copolymer and the THF solution of polyether block amide can be at weight ratios from about 10:1 to about 1:10, in embodiments from about 3:1 to about 1:3.

Forming the wet lubrication film on the surface of the medical instrument may occur by applying the solutions including the components of the wet lubricant film onto the medical instrument after coating with the intermediate film, and then drying, followed by an alkali treatment and drying. The solution for forming the wet lubricant film may be applied a dipping process, similar to the application of the solution for coating the intermediate film. Thereby, the wet lubricant film can be applied at essentially a uniform thickness onto the surface of a base material and/or intermediate film previously applied to the medical instrument. Note, in some embodiments, only a part of the medical instrument may be covered by the intermediate film, so a wet lubricant film can be simultaneously formed on the areas that are not coated with the intermediate film.

Furthermore, application of the solution for forming the wet lubricant film on the medical instrument is not restricted to a dipping process, and any method can be used, similar to the application of the solution for the intermediate film coating. For example, the solution can be applied to the medical instrument using a brush, or can be sprayed on the surface of the medical instrument as a spray. In embodiments, using these methods, the wet lubricant film can be formed selectively only on the areas coated with the intermediate film.

After the solution for forming the wet lubricant film has been applied, the instrument possessing the wet lubricant solution on a portion thereof is dried at a drying temperature from room temperature to about 100° C. in order to remove the solvent. Thereby, a film made of a polymer alloy of methyl vinyl ether maleic anhydride copolymer and polyether block amide is formed on the surface of the medical instrument. The polymer alloy is created when the methyl vinyl ether maleic anhydride copolymer and the polyether block amide are in a macro compatible condition. Note, the drying temperature can be anywhere from room temperature to about 100° C., in embodiments from about 70° C. to about 90° C. Furthermore, the drying time is not particularly restricted, and is determined in combination with the drying temperature. If the drying temperature is from about 70° C. to about 90° C., the drying time may be from about 2 hours to about 4 hours.

The film made of polymer alloy is alkali treated, then water washed, and then dried to form the wet lubricant film. The alkali treatment is performed by dipping the medical instrument in an aqueous solution of an alkali salt such as sodium hydroxide, potassium hydroxide, combinations thereof, or the like, after forming the film made of polymer alloy. By performing the alkali treatment, the carboxyl anhydride groups of the methyl vinyl ether maleic anhydride copolymer in the polymer alloy will react in a neutralizing reaction with the alkali metal to form an alkali salt. Thereby, when the methyl vinyl ether maleic anhydride copolymer alkali salt comes in contact with moisture, the carboxylic acid salt will ionize and better lubricating properties will be demonstrated by the methyl vinyl ether maleic anhydride copolymer. Note, the aqueous solution for the alkali treatment can be any solution that can form an alkali salt of the methyl vinyl ether maleic anhydride copolymer. In embodiments, sodium hydroxide is used. Furthermore, any concentration of the aqueous solution for alkali treatment is acceptable so long as the concentration of the aqueous solution is from about 0.01 N to about 1 N, in embodiments about 0.1 N.

Water washing is performed after the alkali treatment in order to wash away the aqueous solution that was not used during the alkali treatment. In embodiments, washing with flowing distilled water is used. The drying temperature after alkali treatment can be room temperature. Thereby, the wet lubricant film is formed on the surface of the base material of the medical instrument.

By using these methods, a medical instrument with an intermediate film and a wet lubrication film on the surface of the base material of a medical instrument made of metal can be formed. In some embodiments, the method of manufacturing a medical instrument formed with these films as described below.

(1) The solution for the intermediate film coating is produced by dissolving the bisphenol A type epoxy resin prepolymer and the polyamide amine curing agent in a blend of xylene and 1-butanol.

(2) The base material is dipped in the solution for the intermediate film coating.

(3) The base material to which the intermediate film coating has been applied is heated to a temperature from about 50° C. to about 100° C. to remove the solvent, and form the intermediate film coating containing bisphenol A type epoxy resin.

(4) Next, the methyl vinyl ether maleic anhydride copolymer is dissolved in acetone, and optional organic solvent, and the polyether block amide is dissolved in THF, and optional organic solvent, and then both solutions are blended to form the solution for forming the wet lubricant film.

(5) The solution for forming the wet lubricant film is applied to the medical instrument by dipping the surface of the base material where the intermediate film was applied into the solution.

(6) The coated instrument is dried at a temperature from room temperature to about 100° C. to remove the solvent and form a film made of a polymer alloy of polyether block amide and methyl vinyl ether maleic anhydride copolymer.

(7) The instrument having the polymer alloy thereon is dipped in an aqueous solution of sodium hydroxide, for example, to perform an alkali treatment in order to neutralize the film, and then water washing and drying is performed, to obtain a medical instrument with a wet lubricant film formed on the base material.

With a medical instrument formed in this manner, bisphenol A type epoxy resin is used as the intermediate film. Bisphenol A type epoxy resin has functional groups that demonstrate strong adhesion in the chemical structure, and therefore, when cured, the film will be formed with strong adhesion towards the base material made of metal. Therefore, an intermediate film that will not easily be peeled from a base material made of metal can be obtained.

Furthermore, methyl vinyl ether maleic anhydride copolymer that has been alkali treated is used as a component in the wet lubricant film. Because of the action of the methyl vinyl ether maleic anhydride copolymer, the regions where the wet lubricant film is formed on the surface of the medical instrument will become slippery and demonstrate excellent lubricity when the medical instrument is wet, because of contact with physiological saline solution, blood, body fluids, or the like.

Furthermore, the polyether block amide is similarly used as a component in the wet lubricant film. The polyether block amide strongly bonds to the bisphenol A type epoxy resin. Thereby, the polyether block amide will form a polymer alloy with the methyl vinyl ether maleic anhydride copolymer, so the polyether block amide will act as a binder so that the methyl vinyl ether maleic anhydride copolymer can be strongly bonded to the intermediate film. As a result, the wet lubricant film containing methyl vinyl ether maleic anhydride copolymer as a component will not easily be peeled from the intermediate film, and the intermediate film will not easily peel from the metal that is the base material. Therefore, the wet lubricant film itself will not easily peel from the surface of the base material of the medical instrument made of metal.

Furthermore, the methyl vinyl ether maleic anhydride copolymer will not easily elute from the wet lubricant film into physiological saline solution, blood, body fluids, or the like, because the polyether block amide is similarly strongly bonded to the bisphenol A type epoxy resin, and thus the lubricating properties can be maintained for a long period of time. By providing the intermediate film between the base material made of metal and the wet lubricant film, a wet lubricant film with strong adhesion can be obtained as compared to the case where the wet lubricant film is formed as a film directly on the base material made of metal.

In this manner, the present disclosure provides a medical instrument made of metal with a wet lubricant film having excellent lubricity, peel durability, and anti-eluting properties on the surface of the base material used to form the medical instrument. The film coating can be applied using a simple process.

A practitioner such as a doctor or the like can smoothly insert the medical instrument into a body cavity or tissue, and the operation of injecting the medical instrument can be easily performed by the practitioner such as a doctor. In addition, when the medical instrument is inserted by a practitioner such as a doctor, the insertion can be performed without applying excessive force to the medical instrument, and therefore the possibility of injuring areas other than the body insertion area is reduced and the safety is enhanced.

In embodiments, the intermediate film can be coated on either a portion of, or on the entire area of, the medical instrument made of metal. In other words, only the areas of the base material that require coating can be coated. Furthermore, the wet lubricant film can similarly be formed on a part, or the entire area, that is coated by the intermediate film.

In particular, if the metal that composes the medical instrument with lubricity is stainless steel, the adhesion of the intermediate film to the base material will be enhanced, and the peeling durability and non-eluting properties of the wet lubricant film will be further enhanced. Furthermore, if the base material of the medical instrument is a guide wire, the insertion properties into body cavities, tissue, or the like, the push in properties, the tracking properties, and the kink resistant properties, as well as resilience of these properties, will be enhanced and thus the application of the wet lubricant film will act effectively. In particular, if the blood vessel that is the target of insertion of the guide wire is tortuous, or if the distance to the target location is long, the guide wire can be smoothly inserted without losing lubricity part way, and thus the operability and workability will be enhanced for the practitioner.

Furthermore, in accordance with the present disclosure, a bisphenol A type epoxy resin produced by heating the bisphenol A type epoxy resin prepolymer and the polyamide amine-type curing agent was suggested as an intermediate film, and an alkali treated polymer alloy made of methyl vinyl ether maleic anhydride copolymer and polyether block amide was suggested as the wet lubricant film. However these films are not restricted to just these materials, and the films can also be formed by materials that contain these materials. In other words, the composition can include other materials added to the aforementioned materials, which will not cause any problems.

Furthermore, with the manufacturing method for a medical instrument with lubricity according to the present disclosure, excellent lubricity when wet is provided to the surface of a medical instrument made of metal, and a medical instrument having high non-eluting properties and peeling durability of the wet lubricant film can be produced. In embodiments, if the metal that composes the medical instrument with lubricity is stainless steel, or if the base material of the medical instrument with lubricity is a guide wire, a medical instrument with excellent non-eluting properties and peeling durability of the wet lubricating film will be effectively achieved.

The following Examples are being submitted to illustrate embodiments of the present disclosure. These Examples are intended to be illustrative only and are not intended to limit the scope of the present disclosure. Also, parts and percentages are by weight unless otherwise indicated. As used herein, "room temperature" refers to a temperature from about 20° C. to about 25° C. The characteristics of the present disclosure are not restricted to the contents described in the Examples below, and suitable variations are possible within the extent of the technology of the present invention.

EXAMPLES

The initial lubricity, lubricity after abrasion, and lubricity after warm water immersion of films on medical instruments are described below.

Example 1

First, a solvent blend containing xylene and 1-butanol in a 2:1 weight ratio was prepared. Next, bisphenol A type epoxy resin prepolymer (product name: EPICLON 1010-70X (manufactured by DIC), epoxy equivalent weight: 450-500 (g/eq), viscosity: X-Z1 (25° C., Gardener), non-volatile component 69-71 (weight %)) and polyamide amine-type curing agent (product name: LUCKAMIDE N-153-1M-165 (manufactured by DIC), active hydrogen equivalent weight: 472 (g/eq), viscosity: Z2-Z4 (25° C., Gardener), non-volatile component: 64-66 (weight %)) were added to the solvent blend at a weight ratio of 1.5:1 and dissolved and diluted by 7 times the total amount to produce a mixture solution for an intermediate film coating.

The base material of the medical instrument made of metal was immersed in this mixture solution for an intermediate film coating and then immediately withdrawn and heated for 3 hours in an oven at 80° C. The bisphenol A type epoxy resin was thus produced, and an intermediate film made of bisphenol A type epoxy resin was applied and formed on the base material. Note, a guide wire with a 0.035 inch (0.89 mm) diameter with a stainless steel SUS304V metal core wire was used as the base material.

Next, a 2 weight % acetone solution of methyl vinyl ether maleic anhydride copolymer (product name: GANTREZ AN-169, manufactured by ISP (International Specialty Products)) and a 2 weight % THF solution of polyether block amide (product name: PEBAX 2533SA, manufactured by Atochem) were blended at a weight ratio of 1.5:1 to produce a mixture solution for forming a wet lubricant film. The base material coated with the intermediate film described above was immersed in this mixture solution for forming the wet lubricant film, and then removed and dried for 3 hours in an oven at 80° C.

Furthermore, this base material was immersed for 3 minutes in a 0.1 N sodium hydroxide aqueous solution as an alkali treatment, and then removed, water washed, and then dried to form a wet lubricant film on the surface of the base material with the intermediate film therebetween.

Comparative Example 1

For Comparative Example 1, the same wet lubricant film as described above in Example 1 was formed on the same base material as Example 1 without coating with the intermediate film. In other words, the same base material as Example 1, not coated with the intermediate film, was immersed in the same mixture solution for forming a wet lubricant film as Example 1, and then similarly dried and alkali treated to form a wet lubricant film on the surface of the base material.

Comparative Example 2

For Comparative Example 2, the following intermediate film was formed on the same base material as Example 1. Using thinner as a solvent, an epoxy resin prepolymer that was not bisphenol A type (product name: PULCOAT Mild Nonferrous Metal Primer (manufactured by Daido Paint)), a curing agent that was not a polyamide amine-type (product name: PULCOAT Mild Nonferrous Primer Curing Agent (manufactured by Daido Paint)) were added to and dissolved in thinner at a weight ratio of 4:1, and then diluted to 5 times the total amount to produce the mixture solution for intermediate film coating. The base material was coated by the same method as Example 1 with this solution for intermediate film coating, and after coating, a wet lubricant film was formed by the same method as Example 1.

Comparative Example 3

In Comparative Example 3, a guide wire was fabricated using acrylic silicone resin as the material that formed the intermediate film. The following intermediate film was formed on the same base material as Example 1. An acrylic silicone resin solution (product name: PERFECT PRIMER PP201-A (manufactured by ATR)) and an acrylic silicone resin solution (product name: PERFECT PRIMER 201-B (manufactured by ATR)) were blended at a weight ratio of 1:1 to obtain a mixture. This mixture was used to form the intermediate film coating. The base material was coated by the same method as Example 1 with this solution for forming the intermediate film coating, and after coating, a wet lubricant film was formed by the same method as Example 1.

Surface Lubricity Test

Each of the guide wires formed by Example 1 or the Comparative Examples 1 through 3 were tested for initial lubricity, lubricity after abrasion, and lubricity after warm water immersion. Note, the initial lubricity test was a test for confirming that the wet lubricant film that was formed had lubricity.

Furthermore, the lubricity after abrasion test assumed that the guide wire was repeatedly inserted and withdrawn from a blood vessel, for example, and was a test that confirmed the healing durability for maintaining lubricity, even when the guide wire was used in a condition where a fixed stress was applied to the guide wire. Furthermore, the lubricity after warm water immersion test was a test for confirming the anti-eluting properties, where the film components did not elute and the surface lubricity of the film was maintained, even when the guide wire was inserted into a blood vessel and was in contact with blood inside the body for a long period of time.

The evaluation was performed by sliding the guide wire back and forth on the ball of the fingers and expressing the lubricity that was felt using 3 levels. In the evaluation results, "O" indicated a slippery feel with favorable sliding; "Δ" indicated that there was no slippery feel but there was a sliding feel; and "X" indicated that there was no slippery feel and there was no sliding feel.

Test 1

Initial lubricity test: After forming the films, each of the guide wires was immersed for 1 minute in physiological saline solution, and then the guide wires were removed from the physiological saline solution and the lubricity in the area where the film was formed was evaluated.

Test 2

Lubricity after abrasion test: After forming the films, each of the guide wires was immersed for 1 minute in physiological saline solution, and then removed. Next, the area where the film was formed on the guide wire was rubbed back and forth 50 times using the balls of the fingers, and then the guide wire was again immersed in physiological saline solution for 1 minute Furthermore, the guide wire was again removed from the physiological saline solution, and the area that was rubbed back and forth 50 times using the balls of the fingers was touched and the lubricity was evaluated by feel.

Test 3

Lubricity after warm water immersion test: After forming the films, each of the guide wires was immersed for 1 minute in physiological saline solution, and then removed. Next, the area where the film was formed on the guide wire was abraded back and forth 50 times on the balls of the fingers, and then the guide wire was again immersed in physiological saline solution for 1 minute Furthermore, the guide wire was immersed for 24 hours in physiological saline solution at 50° C. Furthermore, the guide wire was again removed from the physiological saline solution, and the area that was rubbed back and forth 50 times using the balls of the fingers was touched and the lubricity was evaluated by feel.

TABLE 1

| | Embodiment | Comparative Example 1 | Comparative Example 2 | Comparative Example 3 |
|---|---|---|---|---|
| Test 1: Initial lubricity | O | O | Δ | O |
| Test 2: Lubricity after abrasion | O | X | X | O |
| Test 3: Lubricity after water immersion | O | X | X | X |

As can be seen from the evaluation results shown in Table 1, the initial lubricity obtained was excellent, and almost at the same level, for the wires of Example 1 and Comparative Examples 1 and 3. In contrast, for Comparative Example 2, there was lubricity, but the level of lubricity was low and a wet lubricant film could not be sufficiently formed. The intermediate film that was used in Comparative Example 2 was thus found to be unsuitable as a base layer for forming the wet lubricant film.

Furthermore, for the lubricity after abrasion, excellent lubricity was achieved even after abrasion of the wires of Example 1 and Comparative Example 3. In contrast, almost no lubricity was achieved for Comparative Examples 1 and 2. This indicates that the wire of Example 1 and Comparative Example 3 demonstrated high peel durability and could maintain the wet lubricant properties without the wet lubricant film peeling off, even from abrasion. In contrast, Comparative Examples 1 and 2 showed that the wet abrasion film was easily peeled off of the base material by abrasion with the balls of the fingers. The results showed that samples where an intermediate film was not formed on the base materials, as with Comparative Example 1, and samples using the intermediate film of Comparative Example 2, had difficulty with peeling durability with regards to abrasion of the wet lubricant film that was formed.

Furthermore, for the lubricity after warm water immersion, excellent lubricity was achieved for the wire of Example 1, even after abrasion and warm water immersion. In contrast, almost no lubricity was achieved for Comparative Examples 1 through 3. This is thought to be because with Comparative Example 1 and Comparative Example 2, the wet lubricant film peeled off after abrasion as described above, and similarly lubricity could not be achieved after warm water immersion. Furthermore, with Comparative Example 3, the wet lubricant film eluted from the base material into the warm water when the base material was immersed in physiological saline solution, and therefore lubricity could not be achieved.

In the lubricity after warm water immersion test, in particular, the component of the film was determined by feeling to have eluted for all of the Comparative Examples, and sufficient surface lubricity could not be obtained because of the eluting, and thus practical use was unlikely. The wire of Example 1, in contrast, had excellent lubricity, and the surface lubricity of the film was maintained even when a stress was repeatedly applied, the wet lubricant film did not peel off, and there was no concern of eluting, so the instrument of the present disclosure had high peeling durability and anti-eluting properties, with high prospects for practical use.

As described above, the wire of Example 1 expressed excellent lubricity in all of Tests 1 through 3, i.e., the film of the wire of Example 1 had excellent initial lubricity, lubricity durability towards abrasion, and anti-eluting properties with regards to warm water immersion. This is because the bonding properties of the polymer alloy containing methyl vinyl ether maleic anhydride copolymer and polyether block amide was enhanced by coating the surface of the base material of the medical instrument made of metal with a bisphenol A type epoxy resin as a base layer, and thus the wet lubricant film exhibited excellent lubricity when wet, and a wet lubricity film with high peeling durability and anti-eluting properties was obtained.

What is claimed is:

1. A medical instrument comprising:
    a base material comprising a metal;
    an intermediate film covering a part of a surface of the base material, the intermediate film comprising a bisphenol A type epoxy resin; and
    a wet lubricant formed on the intermediate film and on an exposed metal surface of the base material, the wet lubricant comprising a polymer alloy comprising a methyl vinyl ether maleic anhydride copolymer and a polyether block amide.

2. The medical instrument according to claim 1, wherein the metal is selected from the group consisting of stainless steel, steel, copper, aluminum, and combinations thereof.

3. The medical instrument according to claim 1, wherein the metal comprises stainless steel.

4. The medical instrument according to claim 1, wherein the medical instrument is selected from the group consisting of guide wires, needles, and stylets.

5. The medical instrument according to claim 1, wherein the medical instrument comprises a guide wire.

6. The medical instrument according to claim 1, wherein the bisphenol A type epoxy resin is produced by reacting a bisphenol A epoxy resin prepolymer and a polyamide amine curing agent.

7. A method for forming a medical instrument comprising:
    providing a base material comprising a metal;
    forming an intermediate coating on at least an exposed metal surface of the base material by applying a solution containing bisphenol A type epoxy resin prepolymer and a polyamide amine-type curing agent in xylene and 1-butanol onto at least a part of the metal;
    heating the bisphenol A type epoxy resin prepolymer and polyamide amine-type curing agent to form an intermediate film comprising a bisphenol A type epoxy resin;
    applying to the intermediate film and on an exposed portion of the metal, a solution for forming a wet lubricant film comprising an acetone solution of methyl vinyl ether maleic anhydride copolymer and a tetrahydrofuran solution of a polyether block amide to form a polymer alloy comprising the methyl vinyl ether maleic anhydride copolymer and the polyether block amide; and
    alkaline processing the polymer alloy to form a wet lubricant film.

8. The method according to claim 7, wherein the metal is selected from the group consisting of stainless steel, steel, copper, aluminum, and combinations thereof.

9. The method according to claim 7, wherein the metal comprises stainless steel.

10. The method according to claim 7, wherein the medical instrument is selected from the group consisting of guide wires, needles, and stylets.

11. The method according to claim 7, wherein the medical instrument comprises a guide wire.

12. The method according to claim 7, wherein heating the bisphenol A type epoxy resin prepolymer and polyamide amine-type curing agent occurs at a temperature of from about 50° C. to about 100° C.

13. The method according to claim 7, wherein heating the bisphenol A type epoxy resin prepolymer and polyamide amine-type curing agent occurs at a temperature of from about 70° C. to about 90° C.

14. The method according to claim 13, wherein heating the bisphenol A type epoxy resin prepolymer and polyamide amine-type curing agent occurs for a period of time from about 2 hours to about 4 hours.

15. The method according to claim 7, wherein the methyl vinyl ether maleic anhydride copolymer is present in the acetone solution at a concentration of from about 0.5 to about 5 percent by weight, and the polyether block amide is present in the tetrahydrofuran solution at a concentration of from about 0.5 to about 5 percent by weight.

16. The method according to claim 7, wherein the ratio of the acetone solution of methyl vinyl ether maleic anhydride copolymer and the tetrahydrofuran solution of polyether block amide is at a weight ratio from about 10:1 to about 1:10.

17. The method according to claim 7, wherein the ratio of the acetone solution of methyl vinyl ether maleic anhydride copolymer and the tetrahydrofuran solution of polyether block amide is at a weight ratio from about 3:1 to about 1:3.

18. The method according to claim 7, wherein the wet lubricant film is dried at a temperature of from about room temperature to about 100° C.

19. The method according to claim 7, wherein the wet lubricant film is dried at a temperature of from about 70° C. to about 90° C. for a period of time from about 2 hours to about 4 hours.

20. The method according to claim 7, wherein alkaline processing the polymer alloy occurs by applying an aqueous solution of an alkali salt selected from the group consisting of sodium hydroxide, potassium hydroxide, and combinations thereof.

21. The method according to claim 20, wherein the aqueous solution of an alkali salt is at a concentration from about 0.01 N to about 1 N.

\* \* \* \* \*